US00PP35017P2

(12) United States Plant Patent
Clark et al.

(10) Patent No.: US PP35,017 P2
(45) Date of Patent: Mar. 7, 2023

(54) PEACH TREE NAMED 'WHITEWATER'

(50) Latin Name: *Prunus persica*
Varietal Denomination: Whitewater

(71) Applicant: THE BOARD OF TRUSTEES OF THE UNIVERSITY OF ARKANSAS, Little Rock, AR (US)

(72) Inventors: John R. Clark, Fayetteville, AR (US); Margaret Worthington, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 17/550,912

(22) Filed: Dec. 14, 2021

(51) Int. Cl.
*A01H 5/08* (2018.01)
*A01H 6/74* (2018.01)

(52) U.S. Cl.
USPC ..... Plt./196
CPC ..... *A01H 6/7463* (2018.05)

(58) Field of Classification Search
USPC ..... Plt./196
CPC ..... A01H 5/0868
See application file for complete search history.

(56) References Cited

U.S. PATENT DOCUMENTS

| | | | |
|---|---|---|---|
| PP15,159 | P3 | 9/2004 | Clark |
| PP17,742 | P3 | 5/2007 | Clark |
| PP17,911 | P3 | 8/2007 | Clark |
| PP22,464 | P3 | 1/2012 | Clark |
| PP26,920 | P3 | 7/2016 | Clark |

OTHER PUBLICATIONS https://www.stuttgartdailyleader.com/arkansas-agricultural-experiment-station-releases-new-white-flesh-peach/; Feb. 25, 2021; 2 pages.*

Beckman, T. G., et al. "Peach tree short life." Southeastern peach growers handbook. University of Georgia, College of Agricultural and Environmental Sciences. Cooperative Extension Service, Athens (2004): 199-205.

Clark, J. R., et al. "'White Diamond' and 'White Cloud' Peaches." HortScience 46.4 (2011): 665-667.

Clark, J. R., et al. "White River Peach." HortScience 38.6 (2003): 1257-1259.

Clark, J. R., et al. "'Souvenirs' Peach." HortScience 48.6 (2013): 800-803.

Clark, J. R., et al. "'White Rock' and 'White County' peaches." HortScience 40.5 (2005): 1561-1565.

Ghiani, A., et al. "Melting of 'Big Top' nectarine fruit: Some physiological, biochemical, and molecular aspects." Journal of the American Society for Horticultural Science 136.1 (2011): 61-68.

Plant Variety Protection 9400013. Peach BY520-9. Issued Jun. 14, 2001.

Sandefur, P. et al. "Peach texture." Horticultural Reviews vol. 41 (2013): 241-302.

University of Arkansas Division of Agriculture Research & Extension. Whitewater Peach flyer. Jan. 2021. Available online at https://cpb-us-e1.wpmucdn.com/wordpressua.uark.edu/dist/3/599/files/2021/01/Whitewater-release-flyer.pdf.

Vauterin, L., et al. "Reclassification of xanthomonas." International Journal of Systematic and Evolutionary Microbiology 45.3 (1995): 472-489.

Worthington, M. and Clark, J.R. (2021). Peach breeding at the University of Arkansas. Acta Hortic. 1304, 21-28.

Worthington, M., et al. "'Effie' Nectarine." HortScience 53.6 (2018): 897-901.

* cited by examiner

*Primary Examiner* — Kent L Bell
(74) *Attorney, Agent, or Firm* — Quarles & Brady LLP

(57) ABSTRACT

A new and distinct peach tree named 'Whitewater' which originated from a hand-pollinated cross of 'White County' (female parent; U.S. Plant Pat. No. 17,742) x 'Souvenirs' peach (male parent; U.S. Plant Pat. No. 26,920) is provided. This new peach tree cultivar can be distinguished by its white, low-acid, slow-melting flesh, early-season ripening, attractive appearance, postharvest performance, and resistance to bacterial spot disease.

3 Drawing Sheets

Latin name: *Prunus persica.*
Varietal denomination: 'Whitewater'.

BACKGROUND

A new and distinct peach tree named 'Whitewater' is described herein. The new cultivar originated from a hand-pollinated cross of 'White County' peach (female parent; U.S. Plant Pat. No. 17,742) x 'Souvenirs' peach (male parent; U.S. Plant Pat. No. 26,920) made in 2008. The seeds resulting from this controlled hybridization were germinated and grown in a greenhouse during the winter of 2008-2009 and were planted in an orchard near Clarksville, Ark. This new cultivar was selected in 2012 for its potential as a fresh-market peach in Arkansas and the mid- to upper-southern United States. 'Whitewater' can be distinguished by its white, low-acid, slow-melting flesh, early-season ripening, attractive appearance, postharvest performance, and resistance to bacterial spot disease.

SUMMARY OF THE INVENTION

The new and distinct peach cultivar originated from a hand-pollinated cross of 'White County' peach (female parent; U.S. Plant Pat. No. 17,742) x 'Souvenirs' (male parent; U.S. Plant Pat. No. 26,920) made in 2008 near Clarksville, Ark. The seeds resulting from this controlled hybridization were germinated in a greenhouse during the winter of 2008-2009 and planted in a field near Clarksville, Ark. The seedlings fruited during the summer of 2012 and one peach seedling, designated Ark. 856, was selected for its slow-melting flesh, early-season ripening, attractive appearance, excellent white peach flavor, and resistance to bacterial spot disease.

The original plant selection was propagated asexually during 2012 at the above-noted location by budding onto the standard peach rootstock cultivar 'Guardian' (BY520-9; U.S. Plant Variety Protection #9,400,013) and a test plot of two plants was established. Subsequently, a larger test planting was established with asexually multiplied plants near Clarksville, Ark. in 2014. Propagation for the larger replicated trial was by budding onto the standard peach rootstock cultivar 'Guardian'® from buds collected at the original Clarksville, Ark. test plot. No incompatibility with peach rootstocks has occurred following budding. During all asexual multiplication, the characteristics of the original plant have been maintained and no aberrant phenotypes have appeared.

The new cultivar has been named 'Whitewater'.

BRIEF DESCRIPTION OF THE PHOTOGRAPHS

The accompanying photographs show typical specimens of the new cultivar in color as nearly true as it is reasonably possible to make in a color illustration of this character.

DETAILED DESCRIPTION OF THE NEW CULTIVAR

Figure 1:
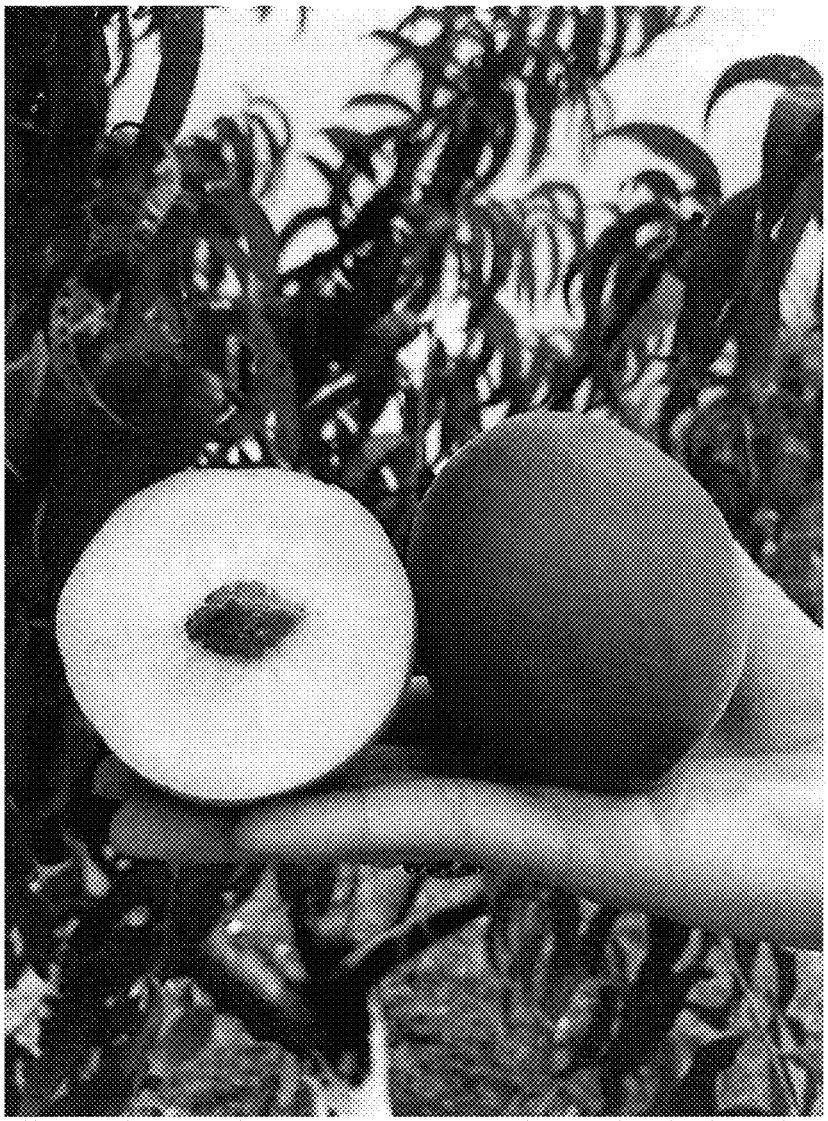
FIG. 1 is a photograph of mature fruit from a 'Whitewater' tree at six years of age.
Figure 2:
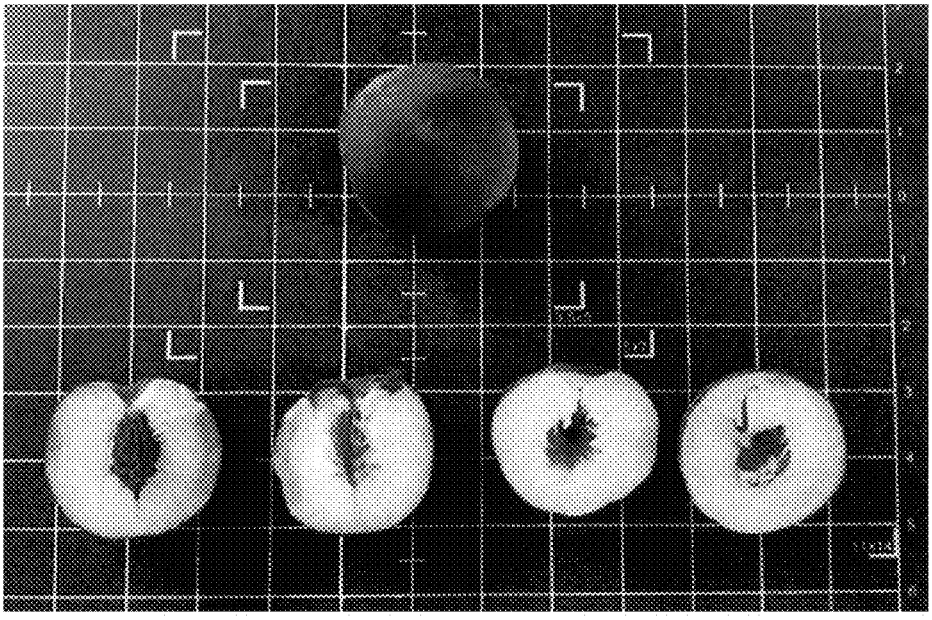
FIG. 2 is a photograph of a whole and longitudinally cut fruit of 'Whitewater' at maturity collected from a tree at six years of age.
Figure 3:
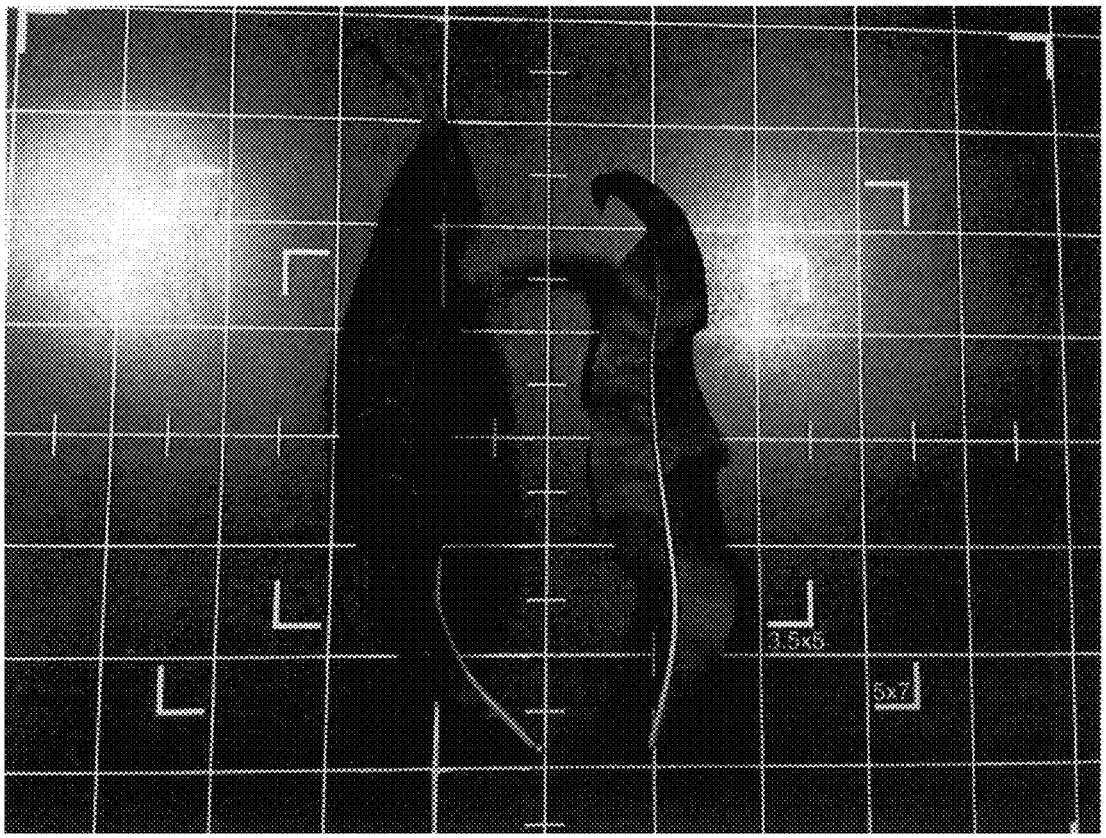
FIG. 3 is a photograph of the adaxial (left) and abaxial (right) sides of mature 'Whitewater' leaves collected from a tree at six years of age.

Plants and fruit of this new cultivar differ phenotypically from its parents. 'Whitewater' and both of its parents, 'White County' (Clark et al., 2005 HortScience 40(5): 1561-1565) and 'Souvenirs' (Clark and Sandefur, 2013 HortScience 48(6): 800-803), have freestone, slow-melting flesh. Also, the fruit of 'Whitewater' and both parents is low-acid. 'Whitewater' differs from its male parent, 'Souvenirs', because 'Souvenirs' has yellow flesh and 'Whitewater' has white flesh. 'Whitewater' also ripens significantly earlier than either parent. The average ripening date of 'Whitewater' in Clarksville, Ark., is one to two weeks before 'Souvenirs' and three to four weeks before 'White County'. Both the parents and the new cultivar are the genus and species *Prunus persica.*

Trees of the new cultivar are moderately vigorous, productive, standard in size, well-branched and symmetrical with a semi-upright growth habit, comparable to other peach trees. Trees express a moderate level of resistance to both foliar and fruit infection of bacterial spot [*Xanthomonas campestris* pv. *pruni* (Smith) Dye]. The new cultivar blooms in the spring on approximately the same date as 'Souvenirs'. No winter cold injury was observed on wood or buds of the new cultivar in Arkansas tests between 2012 and 2020 where minimum temperatures reached 2° F. (−17° C.) during evaluation. However, significant bud damage was observed in spring 2021 after low temperatures reached −15° F. (−26° C.) in February 2021. Chilling requirement to break dormancy is estimated to be 800 hours below 45° F. (7° C.).

Fruit of the new cultivar ripens early-season, averaging 5-10 days before 'White Rock' (U.S. Plant Pat. No. 17,911), one to two weeks before 'Souvenirs' and 'White Cloud' (non-patented), three to four weeks before 'White County' and 'White River' (U.S. Plant Pat. No. 15,159), and four to five weeks before 'White Diamond' (U.S. Plant Pat. No. 22,464) reference cultivars. The average first ripening date is June 27 in west-central Arkansas (Clarksville). Fruit yields have been good and are comparable to the peach cultivars 'White County' and 'Souvenirs'.

The fruit is round in shape. Fruits are attractive with an average 86% bright red blush. The average fruit finish rating of 'Whitewater' was 8.5, higher than the comparison cultivars 'Souvenirs', 'White Cloud', 'White County', 'White Diamond', and 'White River'. The flesh of the fruit is white in color with no red flecking or discoloration. Flesh is of the slow-melting type, crisp at early ripening and soft when fully ripe. The fruit is a freestone, and the flesh separates cleanly from the pit. Fruit size is medium, averaging 170 g, similar to the other early ripening comparison cultivars 'Souvenirs' and 'White Rock'. The fresh fruit has excellent white peach flavor and was rated highly in evaluations. Fruits average 12.7% soluble solids, higher than 'Souvenirs', 'White Cloud', and 'White Rock', but lower than 'White Diamond'. The flavor is sweet with low acidity. The acidity level of 'Whitewater' was 0.18% malic acid, which was similar to 'Souvenirs'.

The following is a detailed description of the botanical and pomological characteristics of the subject peach. Color data are presented in Royal Horticultural Society Colour Chart designations (1986 $2^{nd}$ edition). Where dimensions, sizes, colors and other characteristics are given, it is to be understood that such characteristics are approximations of averages set forth as accurately as practical.

Plants used for botanical data were six years old and grown on a fine sandy loam soil with trickle irrigation near Clarksville, Ark. Trees were trained to an open-center training system and dormant pruned annually. The exception to this is that yield data was collected on trees four years old and trained to a perpendicular V training system. Fruits on all trees were thinned to approximately 6-8 inches between fruits 4-5 weeks after full bloom, The trees were fertilized near budbreak (late March on average) with complete or nitrogen fertilizer. Weeds were controlled with pre- and postemergence herbicides. Routine commercial fungicide and insecticide applications were made to the trees. No bactericides were applied to plantings during testing before fall 2018. Beginning in fall 2018, copper was applied twice annually during dormancy and delayed dormancy to reduce inoculum of bacterial canker (*Pseudomonas syringae* pv. *persicae*) and bacterial spot (*Xanthomonas arboricola* pv. *pruni*). The descriptions reported herein are from specimens grown near Clarksville, Ark.

Plant:

*Size.*—Mature trees (six years of age) average 3.1 m in height and 4.6 m in spread or width, and with a semi-upright growth habit, as grown on 'Guardian'® BY520-9 rootstock using an open-center training system commonly used on peaches. Tree size is comparable to that of the 'Souvenirs' and 'White County' cultivars.

*Growth*.—Moderately vigorous, symmetrical form, good canopy development. Vigor comparable to that of the 'Souvenirs' cultivar.

*Productivity*.—Good productivity and consistent annual bearing from year to year. Fruit is produced on long shoots. Crop load ratings averaged 7,. on a 10-point scale. These ratings were comparable to or higher than those for 'White River', 'White Diamond', 'White Cloud', 'White County', and 'White Rock', though slightly lower than 'Souvenirs' (8.4). Yields from a 2014-planted replicated trial evaluated in 2016-2019 averaged 14.4 kg/tree for 'Whitewater', compared to 15,2 kg/tree for 'Souvenirs', and 17.6 kg/tree for 'White County'.

*Cold hardiness*.—Wood and dormant buds hardy to 2° F. (−17° C.). Wood hardy to −15° F. (−26° C.), but approximately 75% of dormant buds were killed at this temperature.

*Disease resistance*.—Leaves and fruit resistant but not immune to bacterial spot under growing conditions where bacterial spot infection is often very severe on susceptible genotypes. No bactericides were applied to plantings during testing before fall 2018. Beginning in fall 2018, copper was applied twice annually during dormancy and delayed dormancy to reduce inoculum of bacterial canker (*Pseudomonas syringae* pv. *persicae*) and bacterial spot (*Xanthomonas arboricola* pv. *pruni*). The average severity rating for leaf symptoms on 'Whitewater' observational trees was 2.0 out of 5, which was comparable to 'Souvenirs' and better than 'White Cloud', 'White County', 'White Diamond', 'White River', and 'White Rock'. The percent of harvested fruit with bacterial spot was lower than 'Souvenirs', 'White Cloud', 'White County', 'White Diamond', 'White River', and 'White Rock'. One of the 'Whitewater' trees budded on 'Guardian'® rootstock in September 2012 and planted in the breeding observation field in Clarksville, Ark., in spring 2014 began to show symptoms of peach tree short life (PTSL) and bacterial canker in 2016 and this tree was ultimately weakened and blown over during a wind storm in July 2018. Many observation trees budded on 'Guardian'® BY520-9 rootstock established during the same period also exhibited PTSL and bacterial canker symptoms, which are most pronounced in three to seven-year-old trees. The increase in PTSL among new observation trees budded and planted in this period could be due in part to the discontinuation of soil fumigants in the nursery and replanting of peaches in the same breeding observation field over many years. 'Whitewater' is not anticipated to be different in susceptibility to PTSL or bacterial canker compared to most peach cultivars. A commercial fungicide program was utilized in orchards used in the development and evaluation of the instant cultivar, thus no resistance to brown rot (*Monilinia fructicola* (G. Winter) Honey) or scab (*Fusicladium carpophilum* (Thum.) Oudem), the other common diseases at Clarksville, Ark., were determined.

*Insect resistance*.—Insecticides were applied to orchards used in the development of the instant cultivar to control the common insects at the location including oriental fruit moth (*Grapholila molesta* (Busck)), plum curculio (*Conotrachelus nenuphar* (Herbst)), stinkbug (*Halyomorpha halys* (Stal); *Euschistus servus* (Say); *Acrostermum hilare* (Say); *Nezara viridula* (Linnaeus); *Thyanta* spp.), tarnished plant bug (*Lygus lineolaris* (Palisot de Beauvois)), lesser peach tree borer (*Synathedon pictipes* (Grote & Robinson)), and greater peach tree borer (*Synanthedon exitiosa* (Say)). Therefore, no insect resistance was determined in the testing of the instant cultivar.

Foliage/shoots/branches:

*Shoots*.—Smooth. Dormant-season shoot (one-year-old branch): length 116.6 cm; diameter at base 0.6 cm; diameter at midpoint 0.5 cm; diameter at terminal 0.4 cm. Dormant-season shoot color top: Greyed-Purple Group 184A; bottom: Greyed-Orange Group 166D, spurs absent.

*Leaves*.—Simple, alternate, glabrous, lanceolate, petiolate, and deciduous. Venation pinnate; base acute; terminal or apex acuminate; margin serrated. Mature leaves v-shaped in cross-section. Mature leaf size: length 14.2 cm; width midpoint 3.0 cm. Length of blade tip: 3.76 mm. Leaf serrations 5.6/cm. Mature leaf color: abaxial — Yellow-Green Group (146B); adaxial — Green Group (138A). Young leaf color: abaxial — Yellow-Green Group (144B); adaxial — Yellow-Green Group (146C); anthocyanin not present on abaxial or adaxial side of young leaves on midrib or other location. Petiole length — mature leaf: 1.07 cm, petiole width: 1.94 mm; petiole texture: smooth no pubescence; petiole strength: strong; petiole color abaxial: Yellow-Green Group (144A); petiole color adaxial: Green Group (139B). Nectaries: reniform, average of 4.8 per leaf, located at base of leaf blade and top of petiole. Nectaries length: 1.46 mm; nectaries width 1.43 mm; nectary color: Yellow-Green Group (150A). Stipule length: 1.14 cm; stipule width 1.00 mm. Stipule texture: smooth on both sides. Stipule color: abaxial — Yellow Green Group (144B); adaxial — Green Group (143C), shape in cross-section: v-shaped; length of blade tip: 5.27 mm.

*Buds*.—Number of leaf buds per 15 cm: 7.2, evenly distributed along the shoot. Number of flower buds per 15 cm from terminal: 17.2. Mature shoot internode length: base 1.7 cm, midpoint 1.6 cm, terminal 1.3 cm.

Bark (of mature trunk of tree):

*Color*.—Greyed-Orange Group (177A).

*Texture*.—Semi-rough with some parts smooth; no pubescence; lenticels density 5 per $cm^2$; Color of lenticels: Greyed-Orange Group (164C).

Trunk:

*Diameter*.—11.4 cm (at 25 cm above ground level).

Flowers: Bloom occurs prior to vegetative bud break; solitary to occasional double individual flowers at a single node; perfect; self-fertile.

*Floral buds*.—Shape: oval; color: Grey Green Group (197D); length: 0.66 cm; diameter: 0.29 cm.

*Date of bloom*.—First, Julian 77 (March 17); Full, Julian 82 (March 22).

*Size*.—Diameter fully open 4.2 cm; depth 1.5 cm.

*Type*.—Showy.

*Color*.—Abaxial tip: Purple Group (75B); Abaxial center: Red Purple Group (74A); Adaxial tip: Purple Group (75C); Adaxial center: Red Purple Group (74B)

*Sepals*.—Number: 5; length: 5.9 mm; width: 4.4; overall shape: ovate; apex shape: rounded; margin: entire; adaxial color: Red-Purple Group (60B); abaxial color: Green Group (135C).

*Petals*.—Number of petals per flower: 5.2. Length 19.6 mm; width 15.6 mm. Texture: smooth on both abaxial and adaxial surfaces. Shape: overall — elliptic; apex: obtuse; margin: smooth-entire; base: cuneate Petal arrangement: free.

*Pistil*.—Length: 1.7 cm. Color: stigma — Yellow-Green Group (149A); style — Yellow-Green Group (150B). Stigmas parallel with anthers; mostly at even length with anthers.

*Stamens*.—Average 41.6 per flower with pollen present, fertile and abundant. Anthers perpendicular with petals; at even length or slightly longer than petals.

*Pollen color*.—Yellow Group (12B).

*Ovaries*.—Smooth; Color: Grayed-Orange Group (167A).

Fruit:

*Size*.—Medium, avg. 170 g. Diameter stem end 4.2 cm, equator 5.4 cm, blossom end 4.0 cm; length base to apex 5.5 cm.

*Shape*.—Round, symmetrical with no tip.

*Skin*.—Pubescent (peach); not glossy; attractive; ground color: Yellow-Orange Group (20B); blush color: Red Group (46A); Blush description: near solid blush covering about 86% of surface on average; No fruit lenticels.

*Flesh*.—Color: White Group (155A); freestone; uniform slow-melting. Firmness rating of 8.3 (based on 1 to 10 scale with 10 being very firm) which was comparable to 'Souvenirs' (8.4) and 'White County' (8.0).

*Pedicel length*.—0.2 cm.

*Pedicel diameter*.—0.3 cm.

*Pedicel color*.—Greyed-Orange Group (167B).

*Pedicel strength*.—Moderate to strong; holds on well.

*Ripe date*.—June 27 (Julian 178) in west-central Arkansas; 'Souvenirs' ripens one to two weeks later and 'White County' ripens three to four weeks later: harvest period: approximately 10 days; ripening of individual fruit is uniform; last harvest date: July 6 in west-central Arkansas.

*Soluble solids*.—12.7%.

*Fruit juice ph*.—4.95.

*Fruit juice titratable acidity*.—0.18% expressed as malic acid.

*Storage performance*.—Overall ranking for 0-3 weeks of storage for 'Whitewater' was 2.1 slightly better than 'White County' (1.6) and 'Souvenirs' (1.3) on a 5-point scale with 5 being exceptional storage. After three weeks of storage, 'Whitewater' developed negligible meatiness (dry, gel texture) and maintained a high ranking for skin color, skin quality, and flesh color.

Pit/stone:

*Size*.—Length 3.4 cm; diameter (midpoint) 1.7 cm.

*Shape*.—Oval with deep furrowing and pitting.

*Color*.—Red-Purple Group (60A).

*Tendency of pit to split*.—No split pits most years.

Kernel:

*Size*.—Length 1.7 cm; diameter 9.6 mm.

*Shape*.—Oval.

*Color*.—Greyed-Orange Group (163A).

Uses: Fresh consumption, not evaluated for drying or other uses.

THE CULTIVAR

The outstanding characteristics of 'Whitewater' are attractive and flavorful white peach fruit, postharvest storage potential, bacterial spot resistance, and earlier ripening season compared to its parents 'White County' and 'Souvenirs' and other peach releases known to the inventors.

We claim:

1. A new and distinct cultivar of peach tree named 'Whitewater', substantially as illustrated and described.

* * * * *